(12) United States Patent
McCollough et al.

(10) Patent No.: US 8,280,135 B2
(45) Date of Patent: Oct. 2, 2012

(54) SYSTEM AND METHOD FOR HIGHLY ATTENUATING MATERIAL ARTIFACT REDUCTION IN X-RAY COMPUTED TOMOGRAPHY

(75) Inventors: Cynthia H McCollough, Byron, MN (US); Lifeng Yu, Inver Grove Heights, MN (US)

(73) Assignee: MAYO Foundation For Medical Education and Research, Rochester, MN (US)

( * ) Notice: Subject to any disclaimer, the term of this patent is extended or adjusted under 35 U.S.C. 154(b) by 341 days.

(21) Appl. No.: 12/690,765

(22) Filed: Jan. 20, 2010

(65) Prior Publication Data

US 2010/0183214 A1    Jul. 22, 2010

Related U.S. Application Data

(60) Provisional application No. 61/145,924, filed on Jan. 20, 2009.

(51) Int. Cl.
*G06K 9/00* (2006.01)
*A61B 6/00* (2006.01)

(52) U.S. Cl. ............................................ 382/128; 378/4

(58) Field of Classification Search ........................ None
See application file for complete search history.

(56) References Cited

U.S. PATENT DOCUMENTS

| | | | |
|---|---|---|---|
| 4,590,558 A * | 5/1986 | Glover et al. ..................... 378/6 |
| 4,616,318 A * | 10/1986 | Crawford ........................ 378/54 |
| 4,709,333 A * | 11/1987 | Crawford ....................... 600/425 |
| 4,792,900 A * | 12/1988 | Sones et al. ................... 600/407 |
| 5,225,980 A * | 7/1993 | Hsieh et al. ...................... 378/18 |
| 5,243,664 A * | 9/1993 | Tuy ................................ 382/130 |
| 5,615,279 A * | 3/1997 | Yoshioka et al. ............. 382/131 |
| 5,933,471 A * | 8/1999 | Kalvin ............................... 378/4 |
| 6,094,467 A * | 7/2000 | Gayer et al. ...................... 378/4 |
| 6,125,193 A | 9/2000 | Han |
| 6,721,387 B1 | 4/2004 | Naidu et al. |
| 7,444,011 B2 * | 10/2008 | Pan et al. ....................... 382/131 |
| 7,463,712 B2 * | 12/2008 | Zhu et al. .......................... 378/7 |

(Continued)

FOREIGN PATENT DOCUMENTS

WO    2006039809 A1    4/2006

OTHER PUBLICATIONS

Wei et al, "X-ray CT high-density artefact suppression in cryosurgery", Publication Date: Dec. 3, 2002.*

(Continued)

*Primary Examiner* — Manav Seth
(74) *Attorney, Agent, or Firm* — Quarles & Brady, LLP (57) ABSTRACT

The present invention is a method for reducing artifacts caused by highly attenuating materials in x-ray computed tomography ("CT") images. The method includes combining projection views acquired at equivalent view angles to generate a projection plane data set, from which a reformatted projection is produced. The reformatted projection is then processed to detect and segment regions corresponding to objects composed of metals, metal alloys, or other highly attenuating materials. These segmented regions are then removed from the reformatted projection and the removed portions replaced by attenuation information interpolated from portions of the reformatted projection adjacent the removed portions. The interpolated reformatted projection is then mapped back to a projection plane data set, and an image of the subject is reconstructed from the projection views contained in that data set. The reconstructed image, therefore, is one in which artifacts caused by highly attenuating materials are substantially suppressed.

20 Claims, 10 Drawing Sheets

U.S. PATENT DOCUMENTS

2006/0020200 A1* 1/2006 Medow et al. ................ 600/425
2006/0227928 A1 10/2006 Timmer
2006/0293581 A1* 12/2006 Plewes et al. ................ 600/407

OTHER PUBLICATIONS

Bal et al., "Metal artifact reduction in CT using tissue-class modeling and adaptive prefiltering", Publication Date: Jul. 24, 2006.*

De Man et al, An Iterative Maximum-Likelihood Polychromatic Algorithm for CT, IEEE Transactions on Medical Imaging, vol. 20, No. 10, Oct. 2001.

Zhao et al, X-Ray CT Metal Artifact Reduction Using Wavelets: An Application for Imaging Total Hip Prostheses, IEEE Transactions on Medical Imaging, vol. 19, No. 12, Dec. 2000, ;gs 1238-1247.

Kalender et al, Reduction of CT Artifacts Caused by Metallic Impants, Radiology, vol. 164, No. 2, Aug. 1987, pp. 576-577.

Yazdia, et al An Adaptive Approach to Metal Artifact Reduction in Helical Computed Tomography for Radiation Therapy Treatment Planning: Experimental and Clinical Studies, Int. J. Radiation Oncology Biol. Phys., vol. 62, No. 4, pp. 1224-1231, 2005.

Wei et al, X-ray CT high-density artefact suppression in the presence of bones, Institute of Physics Publishing, Physics in Medicine and Biology, Phys. Med. Biol. 49 (2004) 5407-5418.

Mahnken, et al, A New Algorithm for Metal Artifact Reduction in Computed Tomography in Vitro and in Vivo Evaluation After Total Hip Replacement, Investigative Radiology • vol. 38, No. 12, Dec. 2003, pp. 769-775.

Wang, et al, Iterative Deblurring for CT Metal Artifact Reduction, IEEE Transactions on Medical Imaging, Vol. 15, No. 5, Oct. 1996, pp. 657-664.

De Man et al, Reduction of metal streak artifacts in x-ray computed tomography using a transmission maximum a posteriori algorithm, IEEE Transactions on Nuclear Science, vol. 41, No. 3, Jun. 2000, pp. 977-981.

Moseley, et al, Comparison of Localization Performance With Implanted Fiducial Markers and Cone-Beam Computed Tomography for On-Line Image-Guided Radiotherapy of the Prostate, Int. J. Radiation Oncology Biol. Phys., vol. 67, No. 3, pp. 942-953, 2007.

Bazalova et al, Correction of CT artifacts and its influence on Monte Carlo dose calculations, Med. Phys. 34 (6), Jun. 2007, 2007 Am. Assoc. Phys. Med., pp. 2119-2132.

Jaing Hsieha, Adaptive streak artifact reduction in computed tomography resulting from excessive x-ray photon noise, Med. Phys. 25 (11), Nov. 1998, 1998 Am. Assoc. Phys. Med. pp. 2139-2147.

Kachelrieβ et al, Generalized multi-dimensional adaptive filtering for conventional and spiral single-slice, multi-slice, and cone-beam CT, Med. Phys. 28 (4), Apr. 2001, 2001 Am. Assoc. Phys. Med, pp. 475-490.

Glover et al, An algorithm for the reduction of metal clip artifacts in CT reconstruction, Med. Phys. 8(6), Nov./Dec. 1981, Am. Assoc. Phys. Med., pp. 799-807.

Bal et al, Metal artifact reduction in CT using tissue-class modeling and adaptive prefiltering, Med. Phys. 33, 8 . . . , Aug. 2006, 2006 Am. Assoc. Phys. Med., pp. 2852-2859.

Yu et al, A Segmentation-Based Method for Metal Artifact Reduction1, Academic Radiology, vol. 14, No. 4, Apr. 2007, pp. 495-504.

Zhang et al. Reducing Metal Artifacts in Cone-Beam CT Images by Preprocessing Projection Data, Int. J. Radiation Oncology Biol. Phys., vol. 67, No. 3, pp. 924-932, 2007.

Xia, et al, A hybrid approach to reducing computed tomography metal artifacts in intracavitary brachytherapy, Brachytherapy 4 (2005) pp. 18-23.

Williamson et al, Prospects for quantitative computed tomography imaging in the presence of foreign metal bodies using statistical image reconstruction, Med. Phys. 29 (10), Oct. 2002 Am. Assoc. Phys. Med. pp. 2404-2418.

Barber et al, The Quickhull Algorithm for Convex Hulls, ACM Transactions on Mathematical Software, vol. 22, No. 4, Dec. 1996, pp. 469-483.

Watzke et al., A pragmatic approach to metal artifact reduction in CT: merging of metal artifact reduced images, Eur. Radiol (2004), 14:849-856.

\* cited by examiner

SYSTEM AND METHOD FOR HIGHLY ATTENUATING MATERIAL ARTIFACT REDUCTION IN X-RAY COMPUTED TOMOGRAPHY

CROSS-REFERENCE TO RELATED APPLICATIONS

This application claims the benefit of, and incorporates herein by reference in its entirety, U.S. Provisional Patent Application Ser. No. 61/145,924 filed on Jan. 20, 2009, and entitled "System and Method for Metal Artifact Reduction in Computed Tomography."

BACKGROUND OF THE INVENTION

The present invention relates to x-ray computed tomography ("CT") imaging systems and, more particularly, to a method for reducing artifacts resulting from highly attenuating materials in multi-slice helical CT.

In a computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile at a particular view angle.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view," and a "scan" of the object comprises a set of views acquired at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers," or "Hounsfield units", which are used to control the brightness of a corresponding pixel on a display.

The term "generation" is used in CT to describe successively commercially available types of CT systems utilizing different modes of scanning motion and x-ray detection. More specifically, each generation is characterized by a particular geometry of scanning motion, scanning time, shape of the x-ray beam, and detector system.

The so-called third generation scanners use a wide, "divergent" fan beam. In fact, the angle of the beam may be wide enough to encompass most or all of an entire patient section without the need for a linear translation of the x-ray tube and detectors. The x-ray detectors, which form a large array of detectors, are rigidly aligned relative to the x-ray beam, and there are no translational motions at all. The tube and detector array are synchronously rotated about the patient through an angle of around 180-360 degrees. Thus, there is only one type of motion, allowing a much faster scanning time to be achieved. After one rotation, a single tomographic section is obtained.

Cone beam CT systems are similar to so-called third generation 2D CT systems in that the x-ray beam fans out, or diverges, in the plane of the imaging slices. In addition, however, the x-ray beam fans out in the perpendicular direction to acquire attenuation data for a plurality of image slices.

Metal implants are not uncommon in subjects receiving CT examinations and may produce severe image artifacts in the form of bright and dark streaks and dark shadows. Small metal objects that occupy only a small image region can produce artifacts that affect entire images, obscuring anatomical structures and significantly degrading diagnostic value. Metal artifacts arise from the data inconsistency between ideal models assumed by reconstruction algorithms and the actual CT signal, which has been contaminated by the metal, or other highly attenuating material. X-rays are highly attenuated by metals and other materials, which in turn amplifies factors that lead to data inconsistencies and, eventually, artifacts such as noise, beam hardening, scattering, and non-linear partial volume effects.

Noise in projection data may be reduced by increasing the tube output ("mAs") of the x-ray source; however, such an approach delivers an increased radiation dose to a subject and does not correct for other data inconsistencies, including those that lead to streaking and shading artifacts. Image quality may also be improved by increasing the tube potential ("kVp"), which provides higher-energy photons that have improved penetrating capability and reduces beam hardening. While this method is common in scan protocols for subjects having metal implants, it offers minimal improvement in scan quality over scans performed using standard tube potentials.

Adaptive filtering may be used to reduce streaking artifacts caused by photon starvation by adaptively smoothing projection data based on noise level; however, this method cannot correct the severe data inconsistencies caused by highly attenuating materials, such as metals, for example, titanium, cobalt, and stainless steel. Iterative and wavelet methods, which utilize practical data models that characterize noise, beam-hardening, and the scattering processes of protons, have been employed to reduce metal artifacts. While promising, these methods are difficult to implement with the standard reconstruction algorithms in modern CT scanners and can be too computationally expensive for the large data sets generated by multi-slice CT scanners.

Metal artifacts may also be reduced by identifying data contaminated by metal artifacts and replacing it with estimated data. One such method involves segmenting regions containing metal signals in reconstructed images, reprojecting this region to localize metal-contaminated projection data, replacement the affected projection data, and reconstructing the resulting corrected data. This method allows the consistent determination of metal signals among all projection views when the metal region is accurately segmented in the initial reconstructed images. However, severe artifacts in the initial reconstructed images often preclude accurate metal segmentation and prevent effective artifact reduction. Furthermore, reprojection of the metal image to projection space is computationally expensive, especially for the large clinical datasets acquired with multi-slice helical CT, and is sometimes prevented by the unavailability of sufficient information regarding the data acquisition geometry.

Other methods that do not require the reprojection of image data to projection space typically involve the direct segmentation of metal in the projection data and the replacement of metal-contaminated data with values interpolated from neighboring data. Metal segmentation in projection data can be based on a sinusoidal model in the sinogram for small circularly-shaped metal and fan-beam configurations. For example, in circular cone-beam CT geometry, known data acquisition geometry can be used to calculate the track of the metal projections. Such approaches work well for simple data acquisition geometries and simple metal shapes, but these approaches cannot provide effective metal artifact reduction when using complicated data acquisition geometries, for example, multi-slice helical CT, or when imaging complicated metal shapes or anatomical features.

The direct segmentation of metal in projection views acquired using multi-slice helical CT, which are typically composed of matrices having a small longitudinal dimension (for example, 16-64 pixels for typical 16 or 64 slice scanners), is difficult for two primary reasons. First, large quantities of projection data are often acquired to cover a long helical scanning range. Therefore, most projections contain little or no metal content, decreasing a segmentation algorithm's ability to assess the metal content of a projection and segment metal consistently among all projections. Second, the large amount of data acquired during multi-slice helical CT scans, for example, 40,000-60,000 projection views for a typical chest-abdomen-pelvis scan, makes it extremely difficult for a human to review and control the segmentation process.

It would therefore be desirable to develop a method for performing multi-slice helical CT that provides improved reduction of artifacts associated with metals and other highly attenuating materials, increased computational efficiency, and improved control of the artifact reduction process.

SUMMARY OF THE INVENTION

The present invention overcomes the drawbacks of previous methods by providing a method for the reduction of artifacts caused by metals, metal alloys, and other highly attenuating materials when performing computed tomography ("CT") imaging on a subject containing objects composed of such materials. In general, the method includes positioning the subject within a CT imaging apparatus, acquiring a plurality of projection views of the subject at a plurality of view angles, and producing a so-called "reformatted projection" by combining projection views acquired at the same view angle. The method further includes performing pitch-correction to produce a pitch-corrected reformatted projection, identifying regions associated with highly attenuating materials in the pitch-corrected reformatted projection, replacing the identified highly attenuated regions with values interpolated from neighboring regions in the reformatted projection to produce a corrected reformatted projection, and reconstructing from the corrected reformatted projection, images having substantially suppressed artifacts caused by metals and other highly attenuating materials.

The foregoing and other aspects and advantages of the invention will appear from the following description. In the description, reference is made to the accompanying drawings which form a part hereof, and in which there is shown by way of illustration at least one embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1A:
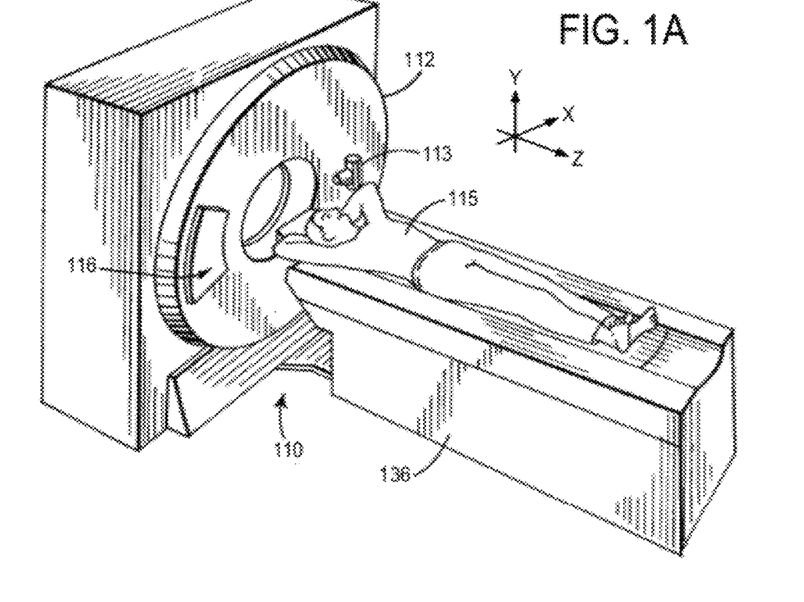
FIG. 1A is a schematic of an exemplary x-ray computed tomography ("CT") imaging system.
Figure 1B:
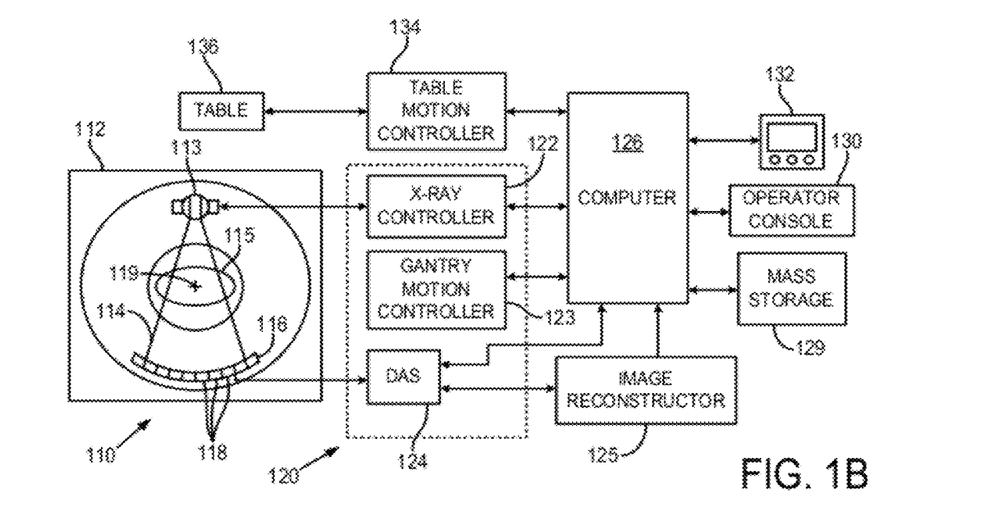
FIG. 1B is a block diagram of an image acquisition system that forms a part of the CT imaging system of FIG. 1A.

With initial reference to FIGS. 1A and 1B, an x-ray computed tomography ("CT") imaging system 110 includes a gantry 112 representative of a "third generation" CT scanner. Gantry 112 has an x-ray source 113 that projects a fan-beam, or cone-beam, of x-rays 114 toward a detector array 116 on the opposite side of the gantry. The detector array 116 is formed by a number of detector elements 118 which together sense the projected x-rays that pass through a medical patient 115. Each detector element 118 produces an electrical signal that represents the intensity of an impinging x-ray beam and hence the attenuation of the beam as it passes through the patient. During a scan to acquire x-ray projection data, the gantry 112 and the components mounted thereon rotate about a center of rotation 119 located within the patient 115.

The rotation of the gantry and the operation of the x-ray source 113 are governed by a control mechanism 120 of the CT system. The control mechanism 120 includes an x-ray controller 122 that provides power and timing signals to the x-ray source 113 and a gantry motor controller 123 that controls the rotational speed and position of the gantry 112. A data acquisition system ("DAS") 124 in the control mechanism 120 samples analog data from detector elements 118 and converts the data to digital signals for subsequent processing. An image reconstructor 125, receives sampled and digitized x-ray data from the DAS 124 and performs high speed image reconstruction. The reconstructed image is applied as an input to a computer 126 which stores the image in a mass storage device 128.

The computer 126 also receives commands and scanning parameters from an operator via console 130 that has a keyboard. An associated display 132 allows the operator to observe the reconstructed image and other data from the computer 126. The operator supplied commands and parameters are used by the computer 126 to provide control signals and information to the DAS 124, the x-ray controller 122 and the gantry motor controller 123. In addition, computer 126 operates a table motor controller 134 which controls a motorized table 136 to position the patient 115 in the gantry 112.

Figure 2:
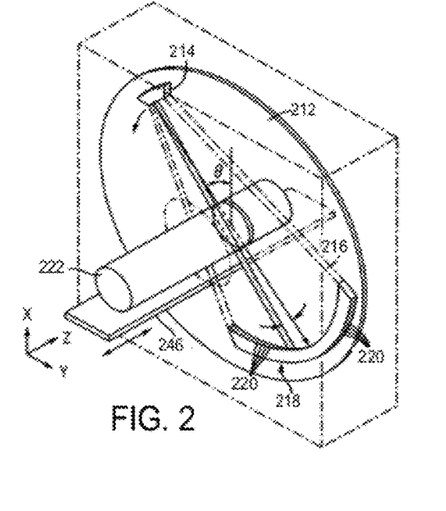
FIG. 2 is a perspective view of an exemplary third generation gantry assembly used in the CT system of FIGS. 1A and 1B.

FIG. 2 illustrates a source-detector assembly 210 which is a specific embodiment of the source-detector assembly 110 shown schematically in FIG. 1B. Assembly 210 illustrates the particular case of a so-called third generation, fan beam CT system. In the assembly 210, a gantry assembly 212 corresponds to the gantry 112 of FIG. 1A. An x-ray source 214 generates a fan beam 216 of x-rays directed toward a detector array 218, which is also affixed to the gantry assembly 212. Array 218 comprises individual detector elements 220 that detect x-rays emitted by source 214. The subject 222, table 246, and subject aperture 248 correspond to subject 122, table 146, and aperture 148 as described with respect to FIG. 1B. In operation, assembly 212 rotates around the z-axis, or "longitudinal axis," passing through subject 222 and perpendicular to the x-y plane. Source 214 can thereby be transported completely around subject 222 along a circular path. Detector array 218, being fixed with respect to source 214, is also transported around subject 222 and thus remains opposite source 214.

Rotation of the gantry assembly 212 around the subject 222 results in x-ray data being acquired by detector elements 220 for a range of view angles, θ. A typical detector array 218 may comprise several hundred individual detector elements 220, such as 888 individual elements 220. The array 218 is positioned on the gantry 212 at a distance of, for example, 0.949 meters ("m") from the x-ray source 214. The circular path of source 214 has a radius of, for example, 0.541 m. Particular values of these parameters are not critical to the present invention and may be varied according to well-known principles of CT system design.

One complete gantry rotation for the gantry 212 may comprise, for example, 984 view angles. Source 214 is thereby positioned to illuminate the subject 222 successively from 984 different directions, θ, and the detector array 218 generates x-ray data at each view angle, θ, from which projection data for 984 separate projection views are acquired.

Figure 3A:
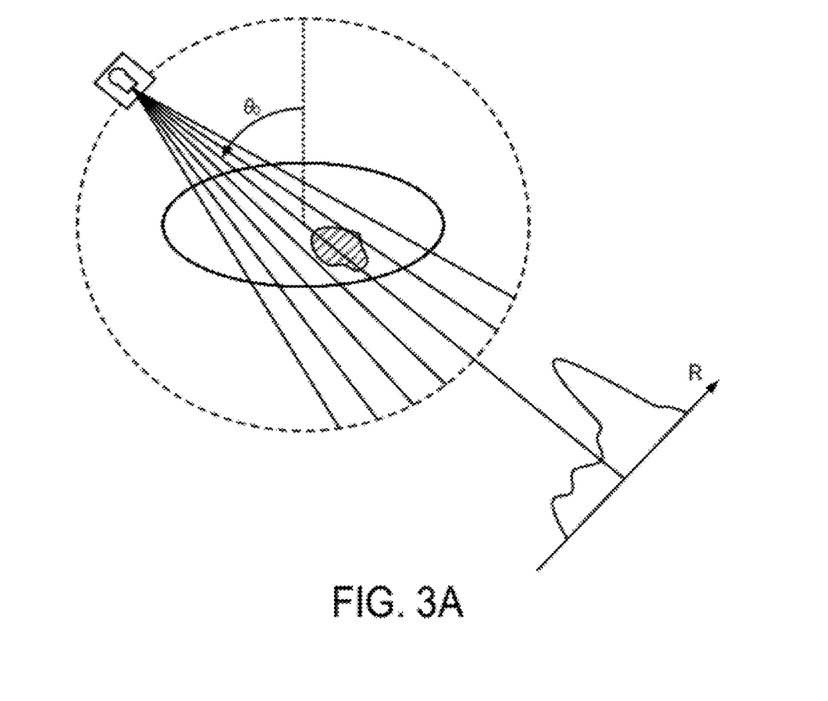
FIG. 3A is a schematic view of an exemplary fan beam projection view acquired with the gantry assembly of FIG. 2.
Figure 3B:
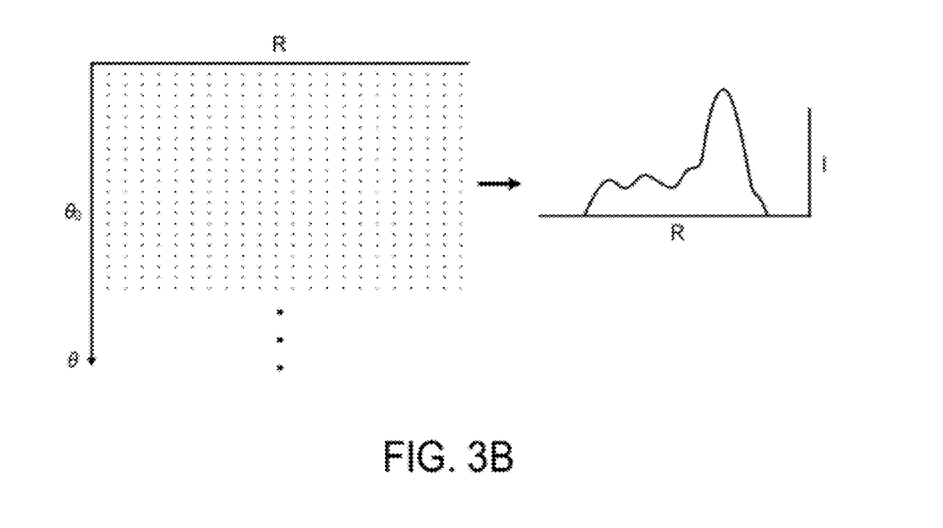
FIG. 3B is a schematic view of an exemplary sinogram data set formed by storing projection views acquired by the CT system of FIGS. 1A and 1B.

In the fan beam case, the data acquisition cycle is sometimes called an axial scan. The projection data for an axial scan is comprised of a set of projection views all acquired at the same axial position, $z_0$. As shown in FIG. 3A, each projection view is acquired at a specific view angle, θ, and each detector attenuation measurement is at a location, R, in the detector array. As shown in FIG. 3B, data from an axial scan may be stored in a two dimensional array called a "sinogram." One dimension of the sinogram corresponds to angular position of the fan beam, or view angle, θ. The other dimension corresponds to positions of the detector elements, R, of the detector array. The detector array in a fan beam CT system, such as array 218 of FIG. 2, generally comprises a single row of detector elements. Therefore, each row of the sinogram corresponds to a discrete view angle, θ, and a single axial position, $z_0$.

A sinogram obtained from an axial scan is a collection of projection views of the subject at the position $z_0$. Here the term "projection view" means such a row of projection data corresponding to a given view angle, θ, and representing the imaged subject at a single axial position, $z_0$. Well known tomographic image reconstruction procedures utilize as their principal inputs a complete set of such projection views, which are discretized in, θ, but all consisting of data values for the same axial position, $z_0$. The projection views are processed by such tomographic techniques to reconstruct a slice image depicting the internal features of the subject in a slice located at the position, $z_0$.

FIG. 3A illustrates the correspondence between a particular view angle, $θ_0$, for the x-ray source and the generation of a well defined row, R, of projection data. In the fan beam case, as noted above, the detector data from the detector array may convert directly into a single row of projection data for a projection view at view angle, $θ_0$. This correspondence results because the detector array provides a single row of detector data representing intensities, I, of the x-rays impinging upon the detector elements. These intensity values, I, indicate attenuation information for the subject at the axial position, $z_0$.

FIG. 3B shows how the projection data for the particular view angle, $θ_0$, is stored in a corresponding row of the sinogram. Each row of this sinogram thus constitutes a projection view that indicates attenuation information, I, for a distinct view angle, $θ_0$, at the same axial position, $z_0$. Once the sinogram is filled with projection views for all the discrete view angles, θ, around the subject, then a suitable CT tomographic image reconstruction algorithm is applied to reconstruct a cross-sectional image of the subject.

Tomographic image data for a three-dimensional representation may comprise image data for several slice images at a succession of axial positions, so-called "stacked 2-D slices" or "stacked slice images." One way to obtain these multiple slice images is to acquire corresponding sinogram data sets slice-by-slice using, for example, a fan beam CT imaging system, such as the system of FIG. 2. However, the preferred method is to use what is called a helical scan.

Helical scanning relaxes the requirement of axial scanning systems that fix the axial position of the gantry at a single z-axis point throughout the data collection cycle. Instead, the entire gantry (source and detector array) translates axially (in the z-direction) relative to the patient while the gantry is being rotated. A single scanning operation, that is, continuous rotation of the gantry, can thereby cover the entire organ or structure under study. The projection views thus acquired may be processed to form a plurality of sinogram data sets at discrete slice locations along the z-axis. Such processing is well known in the art as exemplified by the method disclosed in U.S. Pat. No. 5,270,923 issued on Dec. 14, 1993 and entitled "Computed Tomographic Image Reconstruction Method For Helical Scanning Using Interpolation Of Partial Scans For Image Construction."

Figure 4:
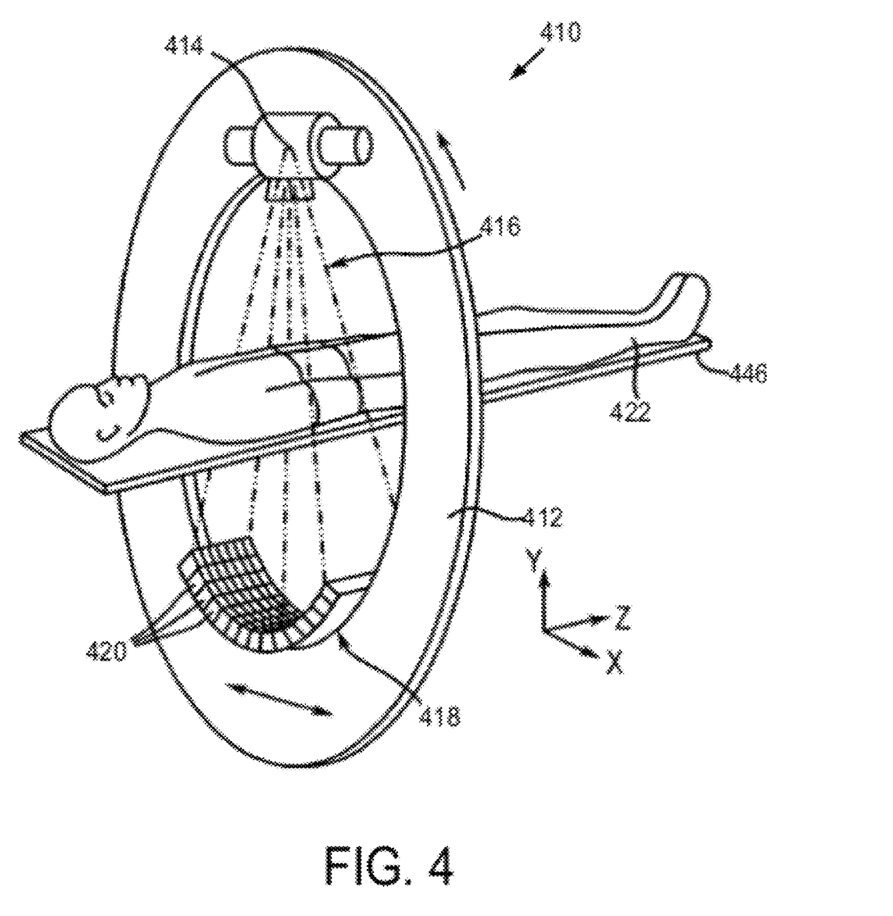
FIG. 4 is a pictorial representation of an exemplary helical scanning CT system including a cone beam x-ray source and a two-dimensional detector array.

FIG. 4 illustrates a source-detector assembly 410 for a desirable alternative to helical fan beam scanning, called helical cone beam scanning. The principal features of assembly 410 are analogous to the components of assemblies 210 in FIG. 2. A gantry 412 supports an x-ray source 414 that generates an imaging x-ray beam 416. However, unlike the fan beam 216 described previously, the beam 416 is a so-called cone beam that spreads, or "fans," in two generally orthogonal directions as the beam is projected away from the source 414.

The assembly 410 of FIG. 4 corresponds to the third generation axial assembly 210 of FIG. 2, in which both the source 414 and the detector array 418 are transported around a subject 422 along respective circular paths as the gantry 412 rotates. Unlike detector array 218, however, the detector array 418 is a so-called multi-row, or two-dimensional detector comprising several rows of detector elements 420. Each row of the array 418 extends circumferentially with respect to the gantry rotation, and the succession of rows extends axially with respect to the gantry z-axis of rotation. The array 418 thereby provides a two dimensional detection area, which corresponds to the spread of the cone beam 416 in two complementary directions. A helical-cone beam CT scanning system provides advantages over the fan beam for acquiring a 3D image. The multi-row detector such as detector array 418 can collect several times more x-ray data during each gantry rotation.

Figure 5A:
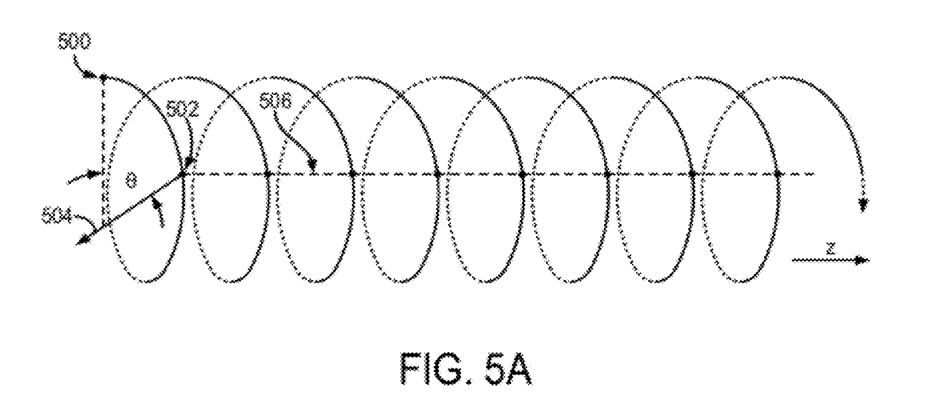
FIG. 5A is a schematic representation of a helical scan path showing the projections selected to form a reformatted projection in accordance with the present invention.

In both fan beam and cone beam helical scanning the x-ray source follows a helical path given by:

$$\theta = \omega t;$$ Eqn. (1)

and, $$z = \left(\frac{p\Delta_d}{2\pi}\right) \cdot \omega t;$$ Eqn. (2)

where $\theta$ is the view angle, z is the axial position of the source, $\omega$ is the rate of gantry rotation, and p is the "pitch," which is the axial translation per gantry rotation, as a fraction of detector collimation $\Delta_d$. The helical path of the x-ray source during a helical scan is illustrated in FIG. 5, discussed below.

As will be appreciated by one of ordinary skill in the art, the above-described systems can be used to perform a number of imaging studies. In accordance with the present invention, the systems may be designated to reduce artifacts caused when imaging a subject containing metals or other highly attenuating materials. As used herein, the term "metal" refers to elemental metals and metalloids; metallic alloys; intermetallic compounds; and other materials containing metals or metalloids. Generally, this is achieved by reformatting the acquired projections to create images from the same angle over the full longitudinal scan range (so-called "reformatted projections"), processing these images to detect image regions containing metals and other highly attenuating materials, and removing the signals corresponding to these significantly high attenuation values from these regions.

Referring particularly now to FIG. 5A, when a helical scan is performed the x-ray source starts at a starting point (z=0, $\theta$=0), as indicated at point 500, and follows a helical path relative to the subject of the examination. At many points along this helical path, projection views are acquired at a succession of view angles, for example ranging over 0 to 360 degrees. In this manner, the projection data from a multi-slice helical scan can be expressed as:

$$P(\alpha,v,\lambda)$$ Eqn. (3);

where $\alpha$ is a detector bin index along a row of the detector, v is a detector bin index along the longitudinal direction, and $\lambda$ is an angular index of the x-ray source, which is related to the longitudinal coordinate of the x-ray source through Eqn. (2) above as:

$$z = \left(\frac{p\Delta_d}{2\pi}\right) \cdot \lambda.$$ Eqn. (4)

Figure 5B:
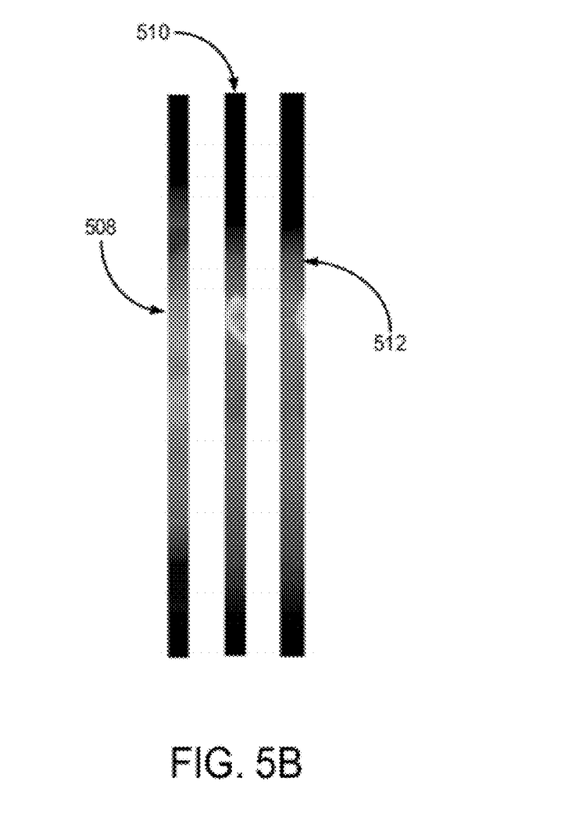
FIG. 5B is an illustration of three exemplary projections acquired during the helical scan of FIG. 5A.

By way of example, if the x-ray source revolves around the subject n times during the helical scan, then n projections are acquired for each given view angle, $\theta$. For example, a projection acquired at a given view angle, $\theta$, during the first gantry revolution, as indicated by point 502, will "see" the subject from the vantage point indicated by arrow 504. During subsequent gantry revolutions, projection views from the same given view angle, $\theta$, will be acquired, as indicated by the points connected by dotted line 506 in FIG. 5A. Referring now to FIG. 5B, three exemplary projections acquired from a helical scan with 32 detector rows are illustrated. These projections were acquired at the same view angle, $\theta$, but at different longitudinal locations, z, during the helical scan. For example, the first projection 508 is expressed as $P(\alpha,v,\theta)$, the second projection 510 is expressed as $P(\alpha,v,\theta+2\pi)$, and the third projection 512 is expressed as $P(\alpha,v,\theta+4\pi)$. This notation is explained in detail below.

It is noted that, in this example, the first projection 508 does not contain any regions corresponding to metal, whereas the second projection and third projections 510 and 512 do contain portions of a metal region. It can be readily appreciated that without the entirety of the metal object present in each projection, a metal segmentation algorithm analyzing each of these projections separately would have difficulties consistently identifying and segmenting the metal regions.

A reformatted projection is created by combing all the projections at each recurrence of a given view angle, $\theta$, every $2\pi$ over the full longitudinal scan range. This process can be generally expressed as:

$$\{P(\alpha,v,\theta+n\cdot 2\pi)|n=1,2,\ldots,N\}$$ Eqn. (5);

where $\theta \in [0,2\pi)$, and N is the total number of rotations for the whole scan range. It is noted that the difference between each of the projections at the given view angle, $\theta$, is the longitudinal location of the x-ray source when they were acquired.

In some embodiments, a reformatted projection is produced by first forming a projection plane data set, $P_\theta$, by selecting and combining all of the projections acquired at the same projection angle, $\theta$, in accordance with Eqn. (5). The reformatted projection is then produced by mapping the individual attenuation measurements in the projection plane data set, $P_\theta$, to a specific pixel location. The attenuation measurements control the intensity of the corresponding pixels in the reformatted projection.

When the reformatted projection is displayed, one sees a two-dimensional projection image of the subject from the selected view angle, $\theta$. The view angle, $\theta$, can be selected to produce a reformatted projection that lies in either the x-z plane or the y-z plane, or many angles therebetween. Reformatted projections can be reconstructed at many different view angles, $\theta$, using the same acquired data sets, and these can be sequentially displayed to rotate the subject.

Figure 5C:
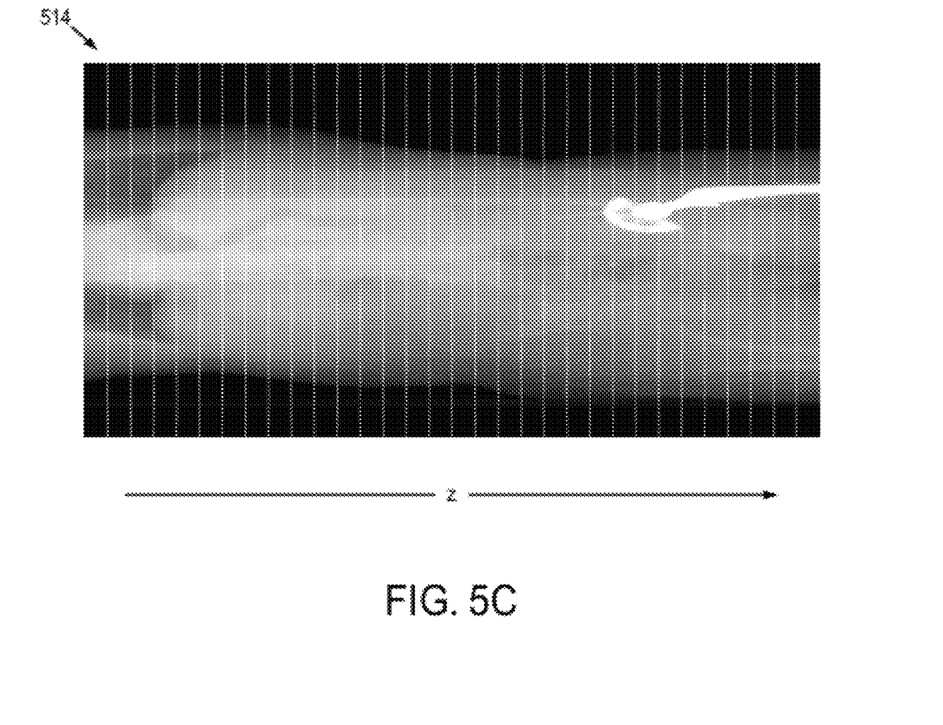
FIG. 5C is an illustration of an exemplary reformatted projection produced from projections acquired during the helical scan of FIG. 5A and in accordance with the present invention.

Referring now to FIG. 5C, an exemplary reformatted projection corresponding to a view angle, $\theta$, and produced from a helical scan with 32 detector rows is illustrated and shown generally at 514. As described above, the reformatted projection 514 is composed of a plurality of individual projections, which are demarcated generally by the vertical dashed lines on the reformatted projection 514. Each successive projection in the reformatted projection corresponds to the projection acquired at the same view angle, $\theta$, recurring in a subsequent revolution of the x-ray source. As described above, this recurrence of the view angle occurs once for each of N complete gantry rotations, each recurrence occurring at a different longitudinal location, z, of the helical scan. It is noted that in the reformatted projection, the presence and the location of the metal object is clear, thereby allowing for more accurate segmentation, as described below in detail.

Figure 6:
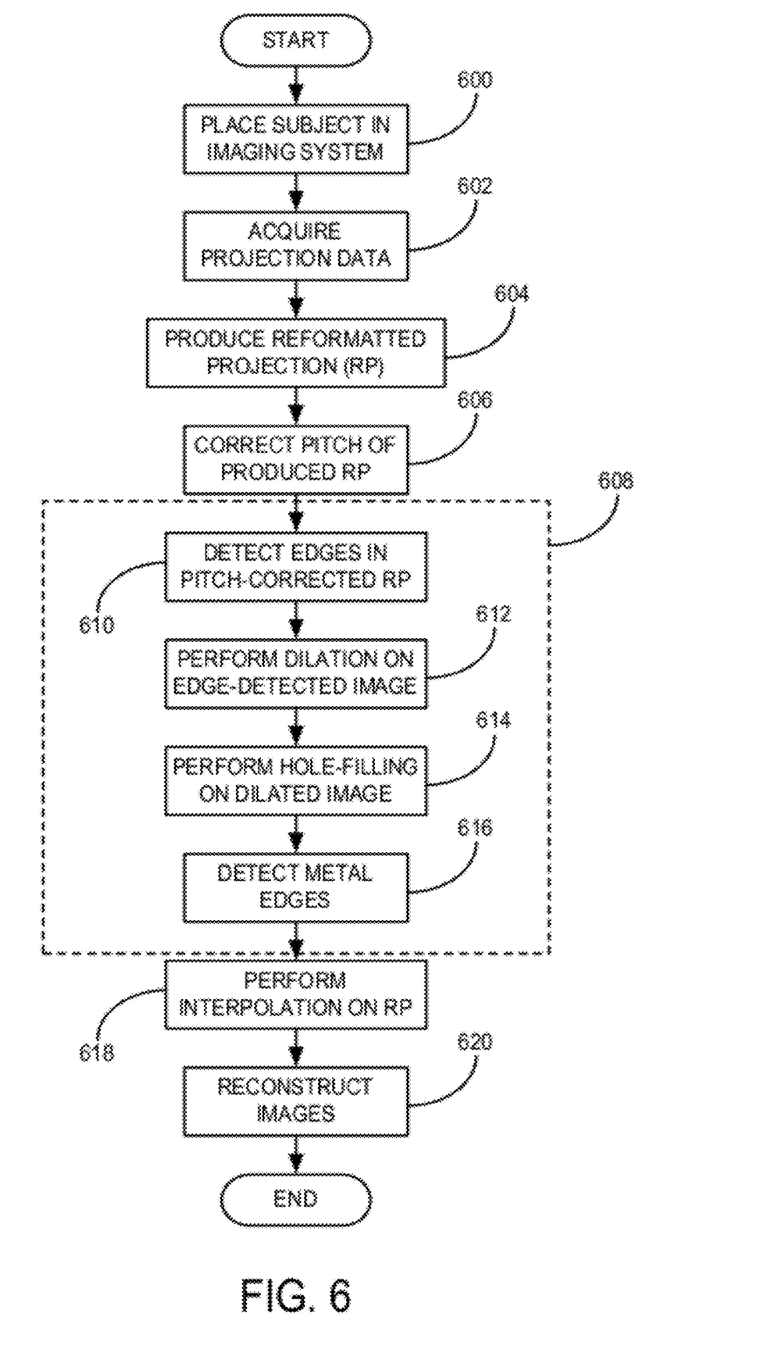
FIG. 6 is a flowchart setting forth the steps of an exemplary artifact reduction process in accordance with the present invention.

Referring now to FIG. 6, a flowchart setting forth the steps of an exemplary method for significantly reducing artifacts caused by metals and other highly attenuating materials from images produced with an x-ray CT system is illustrated. Such a method begins when a subject having a metal implant, other foreign metal object, or other foreign object composed of a highly attenuating material within their body, is positioned within a CT system, as indicated at step 600. Next, projection data is acquired using, for example, a multi-slice helical CT scanning scheme, as indicated at step 602. From the acquired projection data, a reformatted projection is subsequently produced, as indicated at step 604 and described above in detail.

After a reformatted projection is created, the shape of the highly attenuating object might not be continuous due to the pitch factor. Thus, a pitch correction process is performed, as indicated at step 606, to correct for these pitch-related distortions. The pitch factor, p, is the ratio of table feed ("TF") per gantry rotation to section collimation ("SC"), that is, $$p = \frac{TF}{SC}. \quad \text{Eqn. (6)}$$

When p is less than one, there is an overlap for each two adjacent projection views in a reformatted projection. On the other hand, when p is greater than one, there will be a gap between two adjacent projection frames in the reformatted projection. It is generally assumed, however, that p is less than or equal to one, as CT examinations of subjects having metal implants are rarely performed with p greater than one. With the exception of the first and last projection frames in the reformatted projection, there are two overlapping regions in each projection frame. These overlap regions can be expressed as:

$$v \in [0, (1-p) \cdot D] \quad \text{Eqn. (7);}$$

and $$v \in [p \cdot D, D] \quad \text{Eqn. (8).}$$

An undistorted, pitch-corrected reformatted projection is generated by neglecting the data associated with the second overlapping range of each projection frame in a reformatted projection. After pitch correction has been performed, automated highly attenuating material detection and segmentation is performed, as indicated generally at 608.

In general, the highly attenuating material detection and segmentation process may include edge detection; morphological dilation and hole-filling; and segmentation. Thus, methods of feature detection are utilized to segment a region in the reformatted projection that corresponds to a metal object or other object composed of a highly attenuating material. It will be appreciated by those skilled in the art, however, that alternative image processing may be employed to provide improved detection and segmentation of highly attenuating materials.

As indicated at step 610, edge detection is performed on the pitch-corrected virtual image in order to produce an edge-detected image. It is contemplated that edge detection may be performed using, for example, a Sobel operator and an automatically determined initial edge detection threshold to calculate the gradient of each pixel in a pitch-corrected reformatted projection. The magnitude of the edge gradient at each pixel may be compared with the threshold value so that any edge less than the threshold is ignored. For example an edge-detected image including an edge and background is created by performing an edge detection process in which a directional 3×3 kernel is convolved with the reformatted projection. It is further contemplated that, due to the complexity and variety of medical implants, a fully automatic and robust thresholding method may be difficult to implement in some situations. Therefore, the present invention may include a convenient user interface, which will be described later that allows manual adjustment of the threshold.

Referring still to FIG. 6, morphological dilation of the edge-detected image is performed next, as indicated at step 612. For example, a morphological dilation process using a disk shape with a radius of 5 pixels is performed. The area bounded by the edge pixels often contains voids after morphological dilation, and these voids are especially prevalent in larger regions having sharp edges. Therefore, a hole-filling process is performed, as indicated at step 614, to generate regions in the dilated image without interior holes.

Images created by the morphological dilation and hole-filling process often contain several potential highly attenuating regions. Therefore, a highly attenuating region edge-detection process is performed, as indicated at step 616, to produce an image in which highly attenuating regions are segmented. Since metals are typically highly attenuating by nature, the edges of regions containing metals or other highly attenuating materials may be detected by analyzing the potential highly attenuating regions and identifying high-intensity regions in the reformatted projection that generally indicate the presence of a metal or other highly attenuating material. For example, the potential highly attenuating regions in the hole-filled image are compared to the corresponding regions of the reformatted projection. Those potential highly attenuating regions that correspond to a region in the reformatted projection with attenuation values above a selected threshold are thereby selected as highly attenuating material containing regions. It is contemplated that additional highly attenuating material detection and segmentation techniques may be employed to improve the segmentation of highly attenuating regions, especially the segmentation of metal implants constructed of low density materials.

A two-dimensional interpolation process is performed on the segmented image, as indicated at step 618, to remove the highly attenuating regions and replace them with interpolated data, thereby generating a corrected reformatted projection. Improved computational efficiency may be provided by performing interpolation on the highly attenuating region plus a predefined margin, for example, a 10 pixel margin. It is contemplated that two-dimensional interpolation includes methods such as Delaunay triangulation to allow the interpolation of irregularly shaped highly attenuating regions. Following interpolation, image reconstruction is performed on the projection data contained in the corrected reformatted projection, as indicated at step 620. In this manner, an image of the subject having substantially suppressed signals from metals or other highly attenuating materials is produced. Reconstruction may be performed by mapping the corrected reformatted projection back into the original format prior to pitch correction, and loading this data onto the scanner for image reconstruction in the conventional sense.

Figure 7A:
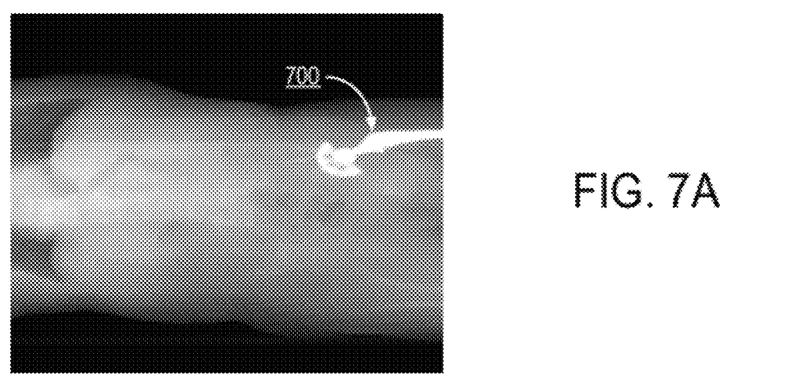
FIG. 7A is an exemplary pitch-corrected reformatted projection of a subject that includes a metal object.

By way of example, and referring now to FIGS. 7A-7G, an exemplary reformatted projection that has been corrected for pitch-induced errors is illustrated in FIG. 7A. The reformatted projection includes a metal object 700. A metal identification algorithm analyzing each of the projections in the reformatted projection separately would have trouble consistently identifying and segmenting the metal object 700. Furthermore, the metal object 700 in the individual projection views is difficult to be identified by visual inspection of a user.

Figure 7B:
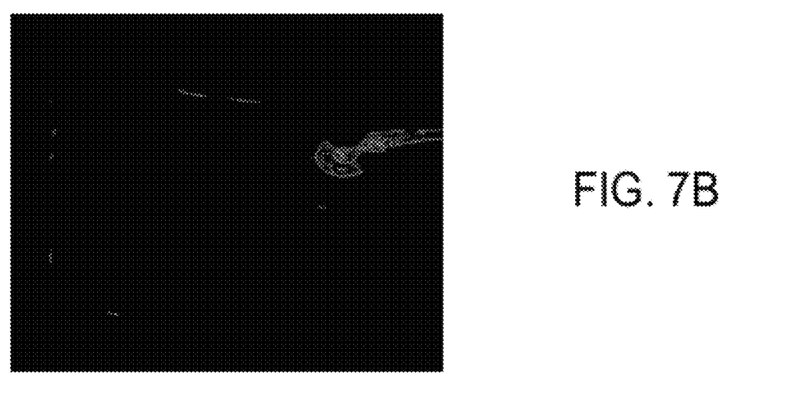
FIG. 7B is an exemplary edge-detected image produced from the exemplary pitch-corrected reformatted projection of FIG. 7A.
Figure 7C:
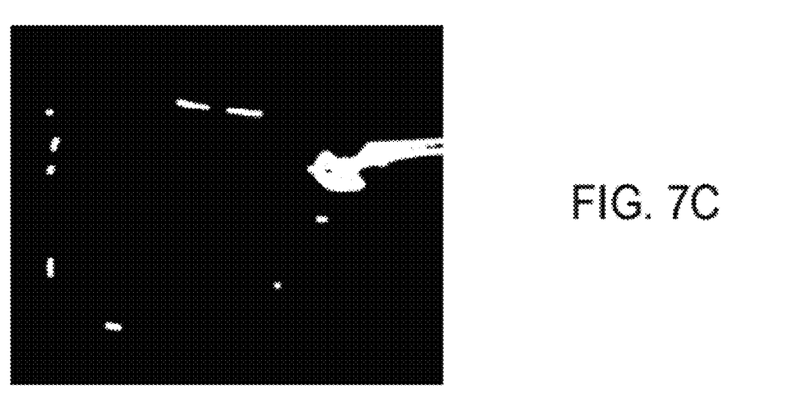
FIG. 7C is an exemplary dilated image produced from the exemplary edge-detected image of FIG. 7B.
Figure 7D:
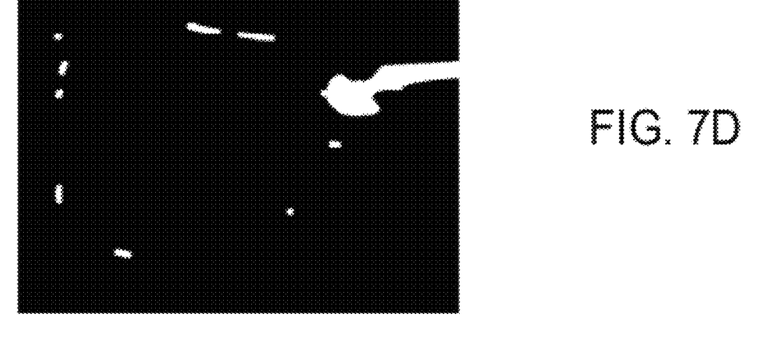
FIG. 7D is an exemplary hole-filled image produced from the exemplary dilated image of FIG. 7C.
Figure 7E:
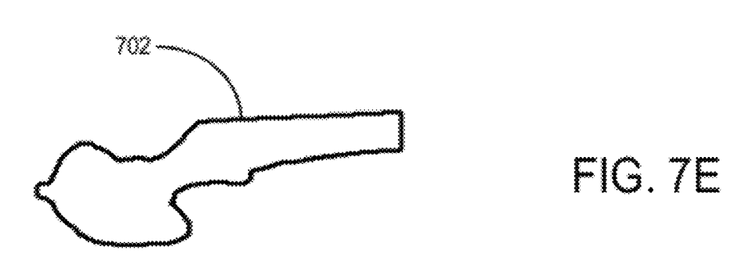
FIG. 7E is a pictorial representation of an exemplary metal object boundary detected and segmented from the exemplary hole-filled image of FIG. 7D.
Figure 7F:
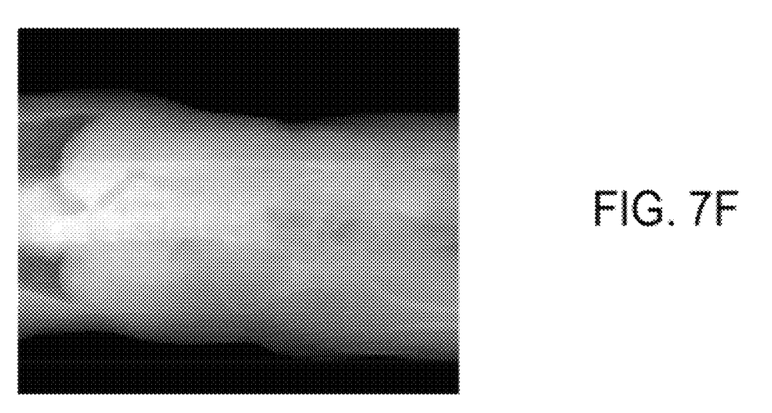
FIG. 7F is an exemplary corrected reformatted projection produced from the exemplary pitch-corrected reformatted projection of FIG. 7A using information about the detected and segmented metal object boundary.

Following edge detection, an edge-detected image corresponding to the reformatted projection is produced, as described above. An exemplary edge-detected image is illustrated in FIG. 7B. This edge-detected image is then dilated, as described above, to produce a dilated image such as the one illustrated in FIG. 7C. Then, the dilated image undergoes a hole-filling process, as described above, to produce a hole-filled image such as the one shown in FIG. 7D. The hole-filled image is then processed to detect and segment metal regions, such as object 700, in the hole-filled image. This detection and segmentation produces, for example, the boundary 702 of the metal object 700, such as the boundary illustrated in FIG. 7E. The location of the metal object 700, as described by the boundary 702, corresponds one-to-one with the reformatted projection; therefore, this information is employed to remove the metal object through interpolation, as described above. The result of the interpolation is a metal-corrected reformatted projection, such as the one illustrated in FIG. 7F.

Figure 7G:
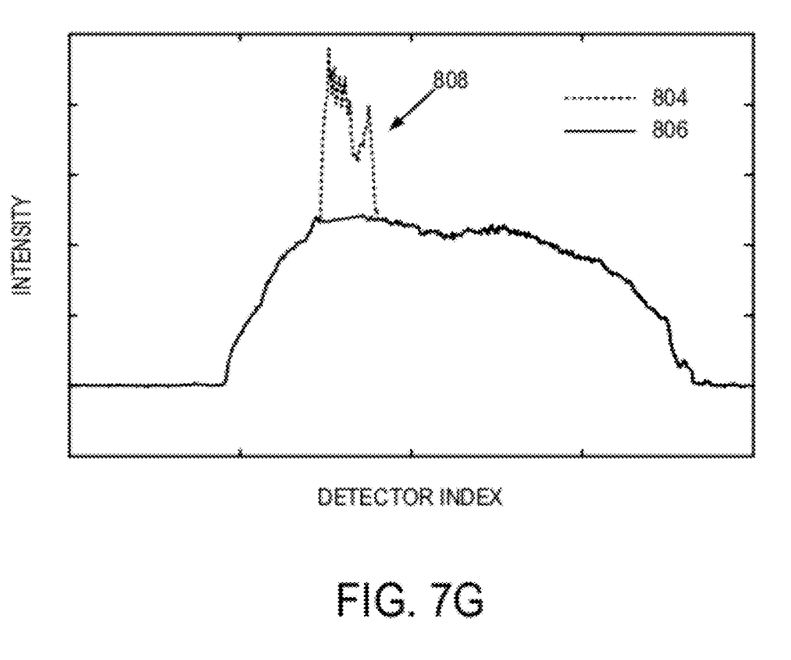
FIG. 7G is an exemplary plot illustrating the intensity along a selected projection in the pitch-corrected reformatted projection of FIG. 7A, and the intensity along the same selected projection in the corrected reformatted projection of FIG. 7F.

A plot of the intensity values in the reformatted projection along a selected line through the metal object 700 is illustrated in FIG. 7G. This plot shows both profile before metal-correction, shown by dashed line 704, and a profile after metal-correction, shown by solid line 706. As can be clearly seen, the high attenuation values associated with the metal object 700, which are indicated generally at arrow 708, are removed by the interpolation process.

It should be noted that, because highly attenuating material detection, segmentation, removal, and interpolation are performed on an entire reformatted projection with the highly attenuating material present, the present invention provides improved computational efficiency over traditional methods. The total number of operations is independent of total scan length and is only dependent on the number of projections acquired per rotation.

It is contemplated that prior information regarding the size, shape, and quantity of metal implants or other foreign objects composed of highly attenuating materials may be used to improve the quality and consistency of the highly attenuating material segmentation and interpolation among different reformatted projections. This is based on the observation that highly attenuating regions in contiguous reformatted projections do not change dramatically. Therefore, information regarding the segmentation of a highly attenuating region in a first reformatted projection can be transferred to subsequent reformatted projections and used as a starting point for segmentation and processing. This use of prior information may provide improved highly attenuating material detection consistency among projections.

The present invention provides improved removal of highly attenuating material signals by allowing accurate detection of projections containing highly attenuating materials at all view angles. To increase the performance of highly attenuating material signal reduction, the present invention may include a user interface that provides a user with feedback regarding the highly attenuating material detection process as the edge detection threshold, which is initially estimated automatically, is adjusted. An exemplary user interface would allow a user to review several reformatted projections over 360 degrees to verify that adequate highly attenuating material detection accuracy is provided. If detection is inaccurate for a particular reformatted projection, the user can adjust the threshold values for that projection. The user may adjust as many projections as necessary and the values may subsequently be used in neighboring projections by interpolation.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing, with an x-ray computed tomography ("CT") system, an image of a subject in which artifacts associated with a highly attenuating material are substantially suppressed, the steps of the method comprising:
   a) acquiring, with the CT system and using a helical-scan with a selected pitch factor, projection data that includes a plurality of projection views of a subject at a plurality of view angles over a selected longitudinal scan range;
   b) producing, from the acquired projection data, a projection plane data set by combining a plurality of projection views from the projection data that were acquired at the same view angle;
   c) producing a reformatted projection by mapping attenuation information in the projection plane data set to an image matrix;
   d) correcting the reformatted projection for errors resulting from the selected pitch factor;
   e) segmenting a region of the corrected reformatted projection that corresponds to an object composed of a highly attenuating material;
   f) removing attenuation information in the segmented region from the corrected reformatted projection;
   g) interpolating attenuation information from portions of the corrected reformatted projection into the segmented region to produce an interpolated reformatted projection; and
   h) producing an image of the subject, in which artifacts caused by highly attenuating materials are substantially suppressed, by mapping the interpolated reformatted projection to a corrected projection plane data set and performing image reconstruction on the projection plane data set.

2. The method as recited in claim 1 in which step e) includes:
   e)i) producing an edge-detected image by performing edge detection on the corrected reformatted projection;
   e)ii) producing a dilated image by performing morphological dilation on the edge-detected image; and
   e)iii) producing a hole-filled image by performing hole-filling on the dilated image.

3. The method as recited in claim 2 in which the hole-filled image is segmented by comparing regions in the hole-filled image with corresponding regions in the corrected reformatted projection.

4. The method as recited in claim 3 in which the regions in the hole-filled image that correspond to regions in the corrected reformatted projection having attenuation values above a selected threshold are selected as the detected region.

5. A method for producing, with an x-ray computed tomography ("CT") system, an image of a subject in which artifacts associated with a highly attenuating material are substantially suppressed, the steps of the method comprising:
   a) acquiring, with the CT system, projection data that includes a plurality of projection views of a subject at a plurality of view angles over a selected longitudinal scan range;

b) producing, from the acquired projection data, a reformatted projection by combining a plurality of projection views from the projection data that were acquired at a common view angle;

c) detecting a region in the produced reformatted projection that corresponds to an object composed of a highly attenuating material;

d) producing a corrected reformatted projection from the produced reformatted projection using the detected region; and e) reconstructing, from the corrected reformatted projection, an image of the subject in which artifacts caused by highly attenuating materials are substantially suppressed.

6. The method as recited in claim 5 in which step c) includes producing a pitch-corrected reformatted projection by correcting for variations in the produced reformatted projection resulting from a pitch of the CT system utilized when acquiring the projection data.

7. The method as recited in claim 5 in which step a) is performed by a helical-scan.

8. The method as recited in claim 5 in which step a) is performed by:
   a)i) acquiring a plurality of projection views of the subject at the plurality of view angles at a longitudinal position; and
   a)ii) repeating step a)i) a plurality of times in order to acquire the projection data, during each repetition acquiring a different plurality of projection views of the subject at the plurality of view angles at a different longitudinal position.

9. The method as recited in claim 5 wherein step c) includes performing at least one of edge detection, morphological dilation, hole-filling, and segmentation.

10. The method as recited in claim 9 in which step c) includes:
   c)i) producing an edge-detected image by performing edge detection on the reformatted projection;
   c)ii) producing a dilated image by performing morphological dilation on the edge-detected image; and
   c)iii) producing a hole-filled image by performing hole-filling on the dilated image.

11. The method as recited in claim 10 in which edge detection is performed in step c)i) using a Sobel operator.

12. The method as recited in claim 10 in which the detected region is detected by segmenting the hole-filled image.

13. The method as recited in claim 12 in which the hole-filled image is segmented by comparing regions in the hole-filled image with corresponding regions in the reformatted projection.

14. The method as recited in claim 13 in which the regions in the hole-filled image that correspond to regions in the reformatted projection having attenuation values above a selected threshold are selected as the detected region.

15. The method as recited in claim 14 in which the selected threshold is 1000 Hounsfield units.

16. The method as recited in claim 5 in which step d) includes removing attenuation information associated with the detected region from the reformatted projection and replacing the removed attenuation information with attenuation information interpolated from portions of the reformatted projection adjacent the detected region.

17. The method as recited in claim 16 in which step d) includes performing interpolation using Delaunay triangulation.

18. The method as recited in claim 5 in which step b) includes:
   b)i) forming a projection plane data set by combining the plurality of projection views from the projection data that were acquired at the same view angle; and
   b)ii) mapping attenuation intensity information in the projection plane data set to an image matrix having a first image matrix index corresponding to a longitudinal position and a second image matrix index corresponding to a detector element.

19. The method as recited in claim 18 in which step e) includes:
   e)i) mapping attenuation information in the corrected reformatted projection to a corrected projection plane data set that includes a plurality of corrected projection views; and
   e)ii) reconstructing the image of the subject from the plurality of corrected projection views.

20. The method as recited in claim 5 in which step e) includes mapping the corrected reformatted projection into a plurality of projection views and reconstructing the image of the subject from the plurality of projection views.

* * * * *